(12) United States Patent
Wang et al.

(10) Patent No.: US 8,382,447 B2
(45) Date of Patent: Feb. 26, 2013

(54) SHUTTLE PUMP WITH CONTROLLED GEOMETRY

(75) Inventors: Zhengyan Wang, Antioch, IL (US); Surya Pratap Rai, Round Lake, IL (US); Ronald H. Spang, Jr., Kenosha, WI (US); Peter Bojan, Grayslake, IL (US); David G. Zabel, Hoffman Estates, IL (US); Joseph Allen Carmichael, Burlington, WI (US); Ralph LaBedz, McHenry, IL (US)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 401 days.

(21) Appl. No.: 12/650,693

(22) Filed: Dec. 31, 2009

(65) Prior Publication Data

US 2011/0158823 A1 Jun. 30, 2011

(51) Int. Cl.
*F04B 43/12* (2006.01)
*F04B 49/06* (2006.01)

(52) U.S. Cl. .......... 417/53; 417/474; 417/479; 604/153

(58) Field of Classification Search .................... 417/53, 417/474, 478, 479; 604/153; 92/92, 91, 92/90; 251/7
See application file for complete search history.

(56) References Cited

U.S. PATENT DOCUMENTS

| | | |
|---|---|---|
| 3,606,596 A | 9/1971 | Edwards |
| 3,756,752 A | 9/1973 | Stenner |
| 3,771,694 A | 11/1973 | Kaminski |
| 3,809,871 A | 5/1974 | Howard et al. |
| 3,951,571 A | 4/1976 | Jung |
| 3,998,103 A | 12/1976 | Bjorklund et al. |
| 4,038,983 A | 8/1977 | Mittleman et al. |
| D246,258 S | 11/1977 | Ekert |
| 4,065,230 A | 12/1977 | Gezari |
| 4,078,562 A | 3/1978 | Friedman |
| 4,151,407 A | 4/1979 | McBride et al. |
| 4,187,057 A | 2/1980 | Xanthopoulos |
| 4,199,307 A | 4/1980 | Jassawalla |

(Continued)

FOREIGN PATENT DOCUMENTS

| | | |
|---|---|---|
| EP | 0215249 | 3/1987 |
| EP | 0426273 A1 | 5/1991 |

(Continued)

OTHER PUBLICATIONS

International Search Report for International Application No. PCT/US 02/36963 of Applicant Baxter International Inc.

(Continued)

*Primary Examiner* — Devon Kramer
*Assistant Examiner* — Ryan Gatzemeyer
(74) *Attorney, Agent, or Firm* — K&L Gates LLP

(57) ABSTRACT

An infusion pump uses an improved shuttle mechanism to more reliably pump liquids in low volumes for medical and other purposes. The improved shuttle uses linear translation and wider, symmetric jaws to grasp infusate tubing and pump liquid infusate through the tubing. Adjustment of the linear motion allows a user to also adjust a pumping volume of the infusion pump. Other shuttles with wider jaws may also pump infusate using a rotary motion. In addition, more than one shuttle, such as two or three shuttles, may be used to approximate continuous pumping. A series of several smaller linear shuttles with sequential actuation may be used as a linear peristaltic pump for general peristaltic pump applications.

9 Claims, 9 Drawing Sheets

U.S. PATENT DOCUMENTS

| | | | |
|---|---|---|---|
| 4,237,409 A | 12/1980 | Sugalski | |
| 4,256,437 A | 3/1981 | Brown | |
| 4,273,121 A | 6/1981 | Jassawalla | |
| 4,276,004 A | 6/1981 | Hahn | |
| 4,277,226 A | 7/1981 | Archibald | |
| 4,308,866 A | 1/1982 | Jelliffe et al. | |
| 4,320,757 A | 3/1982 | Whitney et al. | |
| D263,997 S | 4/1982 | Preussner | |
| 4,332,246 A | 6/1982 | Thomson | |
| 4,369,780 A | 1/1983 | Sakai | |
| 4,373,525 A | 2/1983 | Kobayashi | |
| D268,206 S | 3/1983 | Kosako | |
| 4,392,849 A | 7/1983 | Petre et al. | |
| 4,398,908 A | 8/1983 | Siposs | |
| 4,416,595 A | 11/1983 | Cromie | |
| 4,428,381 A | 1/1984 | Hepp | |
| 4,430,078 A | 2/1984 | Sprague | |
| 4,443,216 A | 4/1984 | Chappell | |
| 4,445,535 A | 5/1984 | Mayfield | |
| 4,447,233 A | 5/1984 | Mayfield | |
| 4,447,234 A | 5/1984 | Mayfield | |
| 4,451,255 A | 5/1984 | Bujan et al. | |
| 4,457,751 A | 7/1984 | Rodler | |
| 4,460,358 A | 7/1984 | Somerville et al. | |
| 4,468,221 A | 8/1984 | Mayfield | |
| 4,472,116 A | 9/1984 | Wenstrup | |
| 4,487,604 A | 12/1984 | Iwatschenko et al. | |
| 4,493,710 A | 1/1985 | King et al. | |
| 4,496,351 A | 1/1985 | Hillell et al. | |
| 4,498,843 A | 2/1985 | Schneider et al. | |
| D278,181 S | 3/1985 | Archibald et al. | |
| 4,504,200 A | 3/1985 | Olson | |
| 4,511,352 A | 4/1985 | Theeuwes et al. | |
| D278,743 S | 5/1985 | Manno et al. | |
| 4,519,792 A | 5/1985 | Dawe | |
| 4,529,401 A | 7/1985 | Leslie et al. | |
| 4,537,561 A | 8/1985 | Xanthopoulos | |
| 4,544,369 A | 10/1985 | Skakoon et al. | |
| 4,551,133 A | 11/1985 | Zegers de Beyl et al. | |
| 4,559,038 A | 12/1985 | Berg et al. | |
| 4,561,830 A | 12/1985 | Bradley | |
| 4,561,856 A | 12/1985 | Cochran | |
| 4,562,751 A | 1/1986 | Nason et al. | |
| 4,565,542 A | 1/1986 | Berg | |
| 4,585,009 A | 4/1986 | Barker et al. | |
| 4,585,941 A | 4/1986 | Bergner | |
| 4,596,550 A | 6/1986 | Troutner | |
| 4,601,702 A | 7/1986 | Hudson | |
| 4,602,249 A | 7/1986 | Abbott | |
| 4,624,661 A | 11/1986 | Arimond | |
| D287,053 S | 12/1986 | Bucchianeri et al. | |
| D287,277 S | 12/1986 | Kosako et al. | |
| 4,637,817 A | 1/1987 | Archibald et al. | |
| 4,639,245 A | 1/1987 | Pastrone et al. | |
| 4,646,781 A | 3/1987 | McIntyre et al. | |
| 4,648,812 A | 3/1987 | Kobayashi et al. | |
| 4,650,469 A | 3/1987 | Berg et al. | |
| 4,652,262 A | 3/1987 | Veracchi | |
| 4,653,987 A | 3/1987 | Tsuji et al. | |
| 4,657,490 A | 4/1987 | Abbott | |
| 4,666,430 A | 5/1987 | Brown et al. | |
| 4,668,220 A | 5/1987 | Hawrylenko | |
| 4,676,776 A | 6/1987 | Howson | |
| 4,678,408 A | 7/1987 | Nason et al. | |
| 4,681,563 A | 7/1987 | Deckert et al. | |
| 4,685,903 A | 8/1987 | Cable et al. | |
| 4,690,673 A | 9/1987 | Bloomquist | |
| 4,696,671 A | 9/1987 | Epstein et al. | |
| D293,468 S | 12/1987 | Hill et al. | |
| 4,714,462 A | 12/1987 | DiDomenico | |
| 4,718,576 A | 1/1988 | Tamura et al. | |
| 4,718,893 A | 1/1988 | Dorman et al. | |
| 4,722,149 A | 2/1988 | Weaver et al. | |
| 4,722,224 A | 2/1988 | Scheller et al. | |
| 4,722,734 A | 2/1988 | Kolln | |
| 4,725,205 A | 2/1988 | Cannon et al. | |
| 4,731,058 A | 3/1988 | Doan | |
| D295,320 S | 4/1988 | Vaughan | |
| 4,741,732 A | 5/1988 | Crankshaw et al. | |
| 4,741,736 A | 5/1988 | Brown | |
| 4,744,786 A | 5/1988 | Hooven | |
| 4,754,401 A | 6/1988 | Kaczynski et al. | |
| 4,756,706 A | 7/1988 | Kerns et al. | |
| 4,758,228 A | 7/1988 | Williams | |
| 4,759,527 A | 7/1988 | Brown | |
| 4,772,263 A | 9/1988 | Dorman et al. | |
| 4,781,548 A | 11/1988 | Alderson et al. | |
| 4,804,368 A | 2/1989 | Skakoon et al. | |
| 4,810,243 A | 3/1989 | Howson | |
| 4,834,704 A | 5/1989 | Reinicke | |
| 4,836,752 A | 6/1989 | Burkett | |
| 4,838,857 A | 6/1989 | Strowe et al. | |
| 4,838,860 A | 6/1989 | Groshong et al. | |
| 4,840,542 A | 6/1989 | Abbott | |
| 4,846,637 A | 7/1989 | Alderson et al. | |
| 4,854,324 A | 8/1989 | Hirschman et al. | |
| 4,856,339 A | 8/1989 | Williams | |
| 4,882,575 A | 11/1989 | Kawahara | |
| D305,060 S | 12/1989 | Bisha' et al. | |
| 4,886,431 A | 12/1989 | Soderquist et al. | |
| 4,890,984 A | 1/1990 | Alderson et al. | |
| 4,898,579 A | 2/1990 | Groshong et al. | |
| 4,900,305 A | 2/1990 | Smith et al. | |
| 4,908,017 A | 3/1990 | Howson et al. | |
| 4,911,168 A | 3/1990 | Davis | |
| 4,919,650 A | 4/1990 | Feingold et al. | |
| 4,923,375 A | 5/1990 | Ejlersen | |
| 4,931,041 A | 6/1990 | Faeser | |
| 4,936,760 A | 6/1990 | Williams | |
| D309,662 S | 7/1990 | Gorton | |
| 4,941,808 A | 7/1990 | Qureshi et al. | |
| 4,943,279 A | 7/1990 | Samiotes et al. | |
| 4,954,046 A | 9/1990 | Irvin et al. | |
| 4,960,230 A | 10/1990 | Marelli | |
| 4,974,464 A | 12/1990 | Erikson et al. | |
| 4,976,151 A | 12/1990 | Morishita | |
| 4,978,335 A | 12/1990 | Arthur, III | |
| 5,000,739 A | 3/1991 | Kulisz et al. | |
| 5,006,050 A | 4/1991 | Cooke et al. | |
| 5,011,378 A | 4/1991 | Brown et al. | |
| 5,017,192 A | 5/1991 | Dodge et al. | |
| 5,034,004 A | 7/1991 | Crankshaw | |
| 5,041,086 A | 8/1991 | Koenig et al. | |
| 5,044,900 A | 9/1991 | Cavallaro | |
| 5,049,047 A | 9/1991 | Polaschegg et al. | |
| 5,053,031 A | 10/1991 | Borsanyi | |
| 5,055,001 A | 10/1991 | Natwick et al. | |
| 5,057,081 A | 10/1991 | Sunderland | |
| 5,061,243 A | 10/1991 | Winchell et al. | |
| D321,559 S | 11/1991 | Kienholz | |
| 5,078,362 A | 1/1992 | Lawless et al. | |
| 5,078,683 A | 1/1992 | Sancoff et al. | |
| 5,080,653 A | 1/1992 | Voss et al. | |
| 5,088,904 A | 2/1992 | Okada | |
| 5,098,256 A | 3/1992 | Smith | |
| 5,098,377 A | 3/1992 | Borsanyi et al. | |
| 5,100,380 A | 3/1992 | Epstein et al. | |
| 5,100,389 A | 3/1992 | Vaillancourt | |
| 5,102,392 A | 4/1992 | Sakai et al. | |
| 5,104,374 A | 4/1992 | Bishko et al. | |
| D326,153 S | 5/1992 | Eastman et al. | |
| 5,116,203 A | 5/1992 | Natwick et al. | |
| 5,120,096 A | 6/1992 | D'Silva | |
| 5,123,275 A | 6/1992 | Daoud et al. | |
| 5,131,816 A | 7/1992 | Brown et al. | |
| D328,952 S | 8/1992 | Arioka | |
| 5,135,500 A | 8/1992 | Zdeb | |
| 5,151,019 A * | 9/1992 | Danby et al. | 417/474 |
| 5,153,827 A | 10/1992 | Coutre et al. | |
| 5,160,320 A | 11/1992 | Yum et al. | |
| 5,165,874 A | 11/1992 | Sancoff et al. | |
| 5,167,633 A | 12/1992 | Mann et al. | |
| 5,176,004 A | 1/1993 | Gaudet | |
| 5,176,644 A | 1/1993 | Srisathapat et al. | |
| 5,181,842 A | 1/1993 | Sunderland et al. | |
| 5,181,910 A | 1/1993 | Scanlon | |
| 5,197,322 A | 3/1993 | Indravudh | |

| | | | | | |
|---|---|---|---|---|---|
| 5,207,645 A | 5/1993 | Ross et al. | 5,472,317 A | 12/1995 | Field et al. |
| 5,213,483 A | 5/1993 | Flaherty et al. | 5,472,420 A | 12/1995 | Campbell |
| 5,217,442 A | 6/1993 | Davis | 5,478,211 A | 12/1995 | Dominiak et al. |
| 5,219,327 A | 6/1993 | Okada | 5,482,446 A | 1/1996 | Williamson et al. |
| 5,219,330 A | 6/1993 | Bollish et al. | 5,485,408 A | 1/1996 | Blomquist |
| 5,219,331 A | 6/1993 | Vanderveen | D367,527 S | 2/1996 | Marston et al. |
| 5,219,428 A | 6/1993 | Stern | D367,528 S | 2/1996 | Marston et al. |
| 5,232,449 A | 8/1993 | Stern et al. | 5,489,265 A | 2/1996 | Montalvo et al. |
| 5,236,416 A | 8/1993 | McDaniel et al. | 5,501,665 A | 3/1996 | Jhuboo et al. |
| 5,238,001 A | 8/1993 | Gallant et al. | 5,503,538 A | 4/1996 | Wiernicki et al. |
| D339,193 S | 9/1993 | Thompson et al. | 5,505,709 A | 4/1996 | Funderburk et al. |
| 5,242,407 A | 9/1993 | Struble et al. | 5,507,412 A | 4/1996 | Ebert et al. |
| 5,242,408 A | 9/1993 | Jhuboo et al. | 5,511,951 A | 4/1996 | O'Leary |
| 5,244,461 A | 9/1993 | Derlien | 5,513,957 A | 5/1996 | O'Leary |
| 5,244,463 A | 9/1993 | Cordner, Jr. et al. | 5,514,103 A | 5/1996 | Srisathapat et al. |
| 5,254,096 A | 10/1993 | Rondelet et al. | 5,520,638 A | 5/1996 | O'Quinn et al. |
| 5,256,157 A | 10/1993 | Samiotes et al. | D371,194 S | 6/1996 | Marston et al. |
| 5,257,971 A | 11/1993 | Lord et al. | 5,522,798 A | 6/1996 | Johnson et al. |
| 5,261,884 A | 11/1993 | Stern et al. | 5,522,799 A | 6/1996 | Furukawa |
| 5,265,431 A | 11/1993 | Gaudet et al. | 5,527,307 A | 6/1996 | Srisathapat et al. |
| D342,231 S | 12/1993 | Walker et al. | 5,529,214 A | 6/1996 | Lasonde et al. |
| 5,276,610 A | 1/1994 | Maeda et al. | 5,531,680 A | 7/1996 | Dumas et al. |
| 5,279,556 A | 1/1994 | Goi et al. | 5,531,697 A | 7/1996 | Olsen et al. |
| 5,281,111 A | 1/1994 | Plambeck et al. | 5,533,981 A | 7/1996 | Mandro et al. |
| 5,290,239 A | 3/1994 | Classey et al. | 5,545,140 A | 8/1996 | Conero et al. |
| 5,295,966 A | 3/1994 | Stern et al. | 5,547,470 A | 8/1996 | Johnson et al. |
| 5,295,967 A | 3/1994 | Rondelet et al. | 5,549,460 A | 8/1996 | O'Leary |
| 5,298,021 A | 3/1994 | Sherer | 5,551,850 A | 9/1996 | Williamson et al. |
| D347,472 S | 5/1994 | Sunderland et al. | 5,554,115 A | 9/1996 | Thomas et al. |
| 5,308,333 A | 5/1994 | Skakoon | 5,554,123 A | 9/1996 | Herskowitz |
| 5,308,335 A | 5/1994 | Ross et al. | 5,562,621 A | 10/1996 | Claude et al. |
| 5,317,506 A | 5/1994 | Coutre et al. | 5,569,186 A | 10/1996 | Lord et al. |
| D348,101 S | 6/1994 | Poli et al. | 5,573,502 A | 11/1996 | LeCocq et al. |
| 5,321,392 A | 6/1994 | Skakoon et al. | 5,573,506 A | 11/1996 | Vasko |
| D348,730 S | 7/1994 | Walker et al. | 5,578,077 A | 11/1996 | Kassatly |
| 5,326,236 A | 7/1994 | Kramer et al. | D376,848 S | 12/1996 | Zeilig et al. |
| 5,328,460 A | 7/1994 | Lord et al. | 5,584,811 A | 12/1996 | Ross et al. |
| 5,330,431 A | 7/1994 | Herskowitz | 5,586,629 A | 12/1996 | Shoberg et al. |
| 5,336,245 A | 8/1994 | Adams et al. | 5,588,815 A | 12/1996 | Zaleski, II |
| 5,338,157 A | 8/1994 | Blomquist | 5,601,420 A | 2/1997 | Warner et al. |
| 5,341,291 A | 8/1994 | Roizen et al. | 5,609,575 A | 3/1997 | Larson et al. |
| 5,343,734 A | 9/1994 | Maeda et al. | 5,620,312 A | 4/1997 | Hyman et al. |
| 5,348,539 A | 9/1994 | Herskowitz | RE35,501 E | 5/1997 | Ross et al. |
| 5,356,379 A | 10/1994 | Vaillancourt | 5,628,619 A | 5/1997 | Wilson |
| D352,778 S | 11/1994 | Irvin et al. | 5,630,710 A | 5/1997 | Tune et al. |
| 5,366,904 A | 11/1994 | Qureshi et al. | D380,260 S | 6/1997 | Hyman |
| D353,667 S | 12/1994 | Tsubota et al. | 5,637,093 A | 6/1997 | Hyman et al. |
| 5,370,612 A | 12/1994 | Maeda et al. | 5,637,095 A | 6/1997 | Nason et al. |
| 5,370,622 A | 12/1994 | Livingston et al. | 5,643,212 A | 7/1997 | Coutre et al. |
| 5,374,251 A | 12/1994 | Smith | 5,647,853 A | 7/1997 | Feldmann et al. |
| 5,374,965 A | 12/1994 | Kanno | 5,647,854 A | 7/1997 | Olsen et al. |
| 5,376,070 A | 12/1994 | Purvis et al. | 5,665,070 A | 9/1997 | McPhee |
| 5,378,231 A | 1/1995 | Johnson et al. | 5,669,877 A | 9/1997 | Blomquist |
| 5,382,236 A | 1/1995 | Otto et al. | 5,673,588 A | 10/1997 | Raymond |
| D355,716 S | 2/1995 | Nash et al. | 5,681,284 A | 10/1997 | Herskowitz |
| 5,387,088 A | 2/1995 | Knapp et al. | 5,681,285 A | 10/1997 | Ford et al. |
| 5,389,078 A | 2/1995 | Zalesky et al. | 5,683,367 A | 11/1997 | Jordan et al. |
| 5,395,320 A | 3/1995 | Padda et al. | 5,685,844 A | 11/1997 | Marttila |
| 5,395,324 A | 3/1995 | Hinrichs et al. | 5,695,464 A | 12/1997 | Viallet |
| 5,395,340 A | 3/1995 | Lee | 5,695,473 A | 12/1997 | Olsen |
| 5,397,222 A | 3/1995 | Moss et al. | D390,654 S | 2/1998 | Alsberg et al. |
| 5,411,482 A | 5/1995 | Campbell | 5,713,856 A | 2/1998 | Eggers et al. |
| 5,415,532 A | 5/1995 | Loughnane et al. | 5,722,957 A | 3/1998 | Steinbach |
| 5,419,684 A | 5/1995 | Struble et al. | 5,741,121 A | 4/1998 | O'Leary |
| 5,423,746 A | 6/1995 | Burkett et al. | 5,743,878 A | 4/1998 | Ross et al. |
| 5,423,759 A | 6/1995 | Campbell | 5,745,378 A | 4/1998 | Barker et al. |
| 5,429,602 A | 7/1995 | Hauser | 5,752,976 A | 5/1998 | Duffin et al. |
| 5,431,627 A | 7/1995 | Pastrone et al. | 5,764,034 A | 6/1998 | Bowman et al. |
| 5,433,704 A | 7/1995 | Ross et al. | 5,766,155 A | 6/1998 | Hyman et al. |
| 5,433,710 A | 7/1995 | VanAntwerp et al. | 5,769,823 A | 6/1998 | Otto |
| D361,379 S | 8/1995 | Sancoff et al. | 5,776,345 A | 7/1998 | Truitt et al. |
| D361,617 S | 8/1995 | Sancoff et al. | 5,782,805 A | 7/1998 | Meinzer et al. |
| 5,437,635 A | 8/1995 | Fields et al. | 5,785,681 A | 7/1998 | Indravudh |
| 5,437,642 A | 8/1995 | Thill et al. | D397,432 S | 8/1998 | Rake et al. |
| 5,458,469 A | 10/1995 | Hauser | 5,788,669 A | 8/1998 | Peterson |
| 5,458,578 A | 10/1995 | Sebesta et al. | 5,791,880 A | 8/1998 | Wilson |
| 5,462,051 A | 10/1995 | Oka et al. | 5,795,327 A | 8/1998 | Wilson et al. |
| 5,462,525 A | 10/1995 | Srisathapat et al. | 5,807,322 A | 9/1998 | Lindsey et al. |
| 5,466,218 A | 11/1995 | Srisathapat et al. | 5,807,336 A | 9/1998 | Russo et al. |

| | | | | | | |
|---|---|---|---|---|---|---|
| 5,813,972 | A | 9/1998 | Nazarian et al. | D475,454 | S | 6/2003 | Gillespie, Jr. et al. |
| 5,814,015 | A | 9/1998 | Gargano et al. | 6,572,604 | B1 | 6/2003 | Platt et al. |
| 5,814,019 | A | 9/1998 | Steinbach et al. | 6,585,675 | B1 | 7/2003 | O'Mahony et al. |
| 5,836,915 | A | 11/1998 | Steinbach et al. | 6,592,551 | B1 | 7/2003 | Cobb |
| 5,840,058 | A | 11/1998 | Ammann et al. | D479,323 | S | 9/2003 | Gillespie, Jr. et al. |
| 5,842,841 | A | 12/1998 | Danby et al. | 6,620,151 | B2 | 9/2003 | Blischak et al. |
| D404,813 | S | 1/1999 | Hauser | 6,648,861 | B2 | 11/2003 | Platt et al. |
| 5,868,710 | A | 2/1999 | Battiato et al. | 6,652,493 | B1 | 11/2003 | Das |
| 5,871,465 | A | 2/1999 | Vasko | 6,656,148 | B2 | 12/2003 | Das et al. |
| 5,885,245 | A | 3/1999 | Lynch et al. | 6,659,980 | B2 | 12/2003 | Moberg et al. |
| D408,911 | S | 4/1999 | Moubayed et al. | 6,666,845 | B2 | 12/2003 | Hooper et al. |
| 5,894,273 | A | 4/1999 | Meador et al. | 6,692,241 | B2 | 2/2004 | Watanabe et al. |
| 5,895,371 | A | 4/1999 | Levitas et al. | 6,755,814 | B2 | 6/2004 | Wieland et al. |
| 5,897,530 | A | 4/1999 | Jackson | 6,776,773 | B2 | 8/2004 | Kiyatake et al. |
| 5,904,668 | A | 5/1999 | Hyman et al. | 6,800,069 | B2 | 10/2004 | Lampropoulos et al. |
| 5,908,414 | A | 6/1999 | Otto et al. | 6,805,687 | B2 | 10/2004 | Dextradeur et al. |
| 5,935,099 | A | 8/1999 | Peterson et al. | 6,827,702 | B2 | 12/2004 | Lebel et al. |
| 5,935,106 | A | 8/1999 | Olsen | 6,854,620 | B2 | 2/2005 | Ramey |
| 5,943,633 | A | 8/1999 | Wilson et al. | 6,945,954 | B2 | 9/2005 | Hochman et al. |
| 5,951,510 | A | 9/1999 | Barak | 6,999,854 | B2 | 2/2006 | Roth |
| 5,954,696 | A | 9/1999 | Ryan | 7,008,403 | B1 | 3/2006 | Mallett |
| 5,954,697 | A | 9/1999 | Srisathapat et al. | 7,018,361 | B2 | 3/2006 | Gillespie, Jr. et al. |
| 5,957,890 | A | 9/1999 | Mann et al. | 7,022,107 | B1 | 4/2006 | Christensen et al. |
| 5,988,983 | A | 11/1999 | Furusawa | 7,025,226 | B2 | 4/2006 | Ramey |
| 5,993,420 | A | 11/1999 | Hyman et al. | 7,029,455 | B2 | 4/2006 | Flaherty |
| 6,004,020 | A | 12/1999 | Bartur | 7,092,796 | B2 | 8/2006 | Vanderveen |
| 6,013,057 | A | 1/2000 | Danby et al. | 7,182,750 | B2 | 2/2007 | Lampropoulos et al. |
| D420,737 | S | 2/2000 | Kivlehan | 7,193,521 | B2 | 3/2007 | Moberg et al. |
| 6,024,539 | A | 2/2000 | Blomquist | 7,232,423 | B2 | 6/2007 | Mernoe |
| 6,078,273 | A | 6/2000 | Hutchins et al. | 7,236,936 | B2 | 6/2007 | White et al. |
| 6,083,201 | A | 7/2000 | Skinkle | 7,255,683 | B2 | 8/2007 | Vanderveen et al. |
| D430,288 | S | 8/2000 | Mason et al. | 7,306,578 | B2 | 12/2007 | Gray et al. |
| D430,289 | S | 8/2000 | Mason et al. | 7,322,961 | B2 | 1/2008 | Forrest |
| 6,095,757 | A | 8/2000 | Frezza | 7,338,464 | B2 | 3/2008 | Blischak et al. |
| 6,106,498 | A | 8/2000 | Friedli et al. | 7,341,581 | B2 | 3/2008 | Mallett |
| 6,110,152 | A | 8/2000 | Kovelman | 7,347,837 | B2 | 3/2008 | Azzolini |
| 6,123,524 | A | 9/2000 | Danby et al. | 7,351,226 | B1 | 4/2008 | Herskowitz |
| 6,129,517 | A | 10/2000 | Danby et al. | 7,356,382 | B2 | 4/2008 | Vanderveen |
| 6,135,949 | A | 10/2000 | Russo et al. | 7,374,556 | B2 | 5/2008 | Mallett |
| 6,139,748 | A | 10/2000 | Ericson et al. | D574,016 | S | 7/2008 | Yodfat et al. |
| D434,142 | S | 11/2000 | Cheney, II et al. | D577,118 | S | 9/2008 | Yodfat et al. |
| 6,145,695 | A | 11/2000 | Garrigues | 7,471,994 | B2 | 12/2008 | Ford et al. |
| 6,173,198 | B1 | 1/2001 | Schulze et al. | 7,534,226 | B2 | 5/2009 | Mernoe et al. |
| RE37,074 | E | 2/2001 | Danby et al. | 7,559,926 | B1 | 7/2009 | Blischak |
| 6,195,887 | B1 | 3/2001 | Danby et al. | 7,569,030 | B2 | 8/2009 | Lebel et al. |
| 6,203,528 | B1 | 3/2001 | Deckert et al. | 7,601,148 | B2 | 10/2009 | Keller |
| 6,213,723 | B1 | 4/2001 | Danby et al. | 7,608,060 | B2 | 10/2009 | Gillespie, Jr. et al. |
| 6,213,738 | B1 | 4/2001 | Danby et al. | 7,611,498 | B2 | 11/2009 | Hasler |
| 6,213,739 | B1 * | 4/2001 | Phallen et al. ............... 417/478 | 7,621,893 | B2 | 11/2009 | Moberg et al. |
| 6,231,560 | B1 | 5/2001 | Bui et al. | 7,632,249 | B2 | 12/2009 | Momeni et al. |
| 6,269,340 | B1 | 7/2001 | Ford et al. | 7,637,892 | B2 | 12/2009 | Steinbach et al. |
| D446,854 | S | 8/2001 | Cheney, II et al. | 7,647,237 | B2 | 1/2010 | Malave et al. |
| 6,270,478 | B1 | 8/2001 | Mernøe | D612,484 | S | 3/2010 | Yodfat et al. |
| 6,280,416 | B1 | 8/2001 | Van Antwerp et al. | D614,587 | S | 4/2010 | Yodfat et al. |
| D447,558 | S | 9/2001 | Cartledge et al. | 7,708,717 | B2 | 5/2010 | Estes et al. |
| 6,297,795 | B1 | 10/2001 | Kato et al. | 7,717,903 | B2 | 5/2010 | Estes et al. |
| 6,305,908 | B1 | 10/2001 | Hermann et al. | 7,725,272 | B2 | 5/2010 | Ginggen et al. |
| D453,830 | S | 2/2002 | McDowell et al. | 7,743,975 | B2 | 6/2010 | Miller |
| 6,347,553 | B1 | 2/2002 | Morris et al. | 7,758,552 | B2 | 7/2010 | Zoltan et al. |
| 6,348,043 | B1 | 2/2002 | Hagen et al. | 7,766,863 | B2 | 8/2010 | Gillespie, Jr. et al. |
| 6,348,952 | B1 | 2/2002 | Jeong | 7,766,873 | B2 | 8/2010 | Moberg et al. |
| 6,358,225 | B1 | 3/2002 | Butterfield | 7,776,029 | B2 | 8/2010 | Whitehurst et al. |
| D457,949 | S | 5/2002 | Krug et al. | 7,776,030 | B2 | 8/2010 | Estes et al. |
| 6,398,760 | B1 | 6/2002 | Danby | 7,789,859 | B2 | 9/2010 | Estes et al. |
| 6,413,239 | B1 | 7/2002 | Burns et al. | 7,794,426 | B2 | 9/2010 | Briones et al. |
| 6,423,035 | B1 | 7/2002 | Das et al. | 7,794,427 | B2 | 9/2010 | Estes et al. |
| D461,241 | S | 8/2002 | Moberg et al. | 7,794,428 | B2 | 9/2010 | Estes et al. |
| D461,891 | S | 8/2002 | Moberg | 7,803,134 | B2 | 9/2010 | Sharifi et al. |
| D462,121 | S | 8/2002 | Cartledge et al. | 7,833,196 | B2 | 11/2010 | Estes et al. |
| 6,458,102 | B1 | 10/2002 | Mann et al. | 7,837,651 | B2 | 11/2010 | Bishop et al. |
| 6,471,436 | B1 | 10/2002 | Gjata et al. | 7,850,641 | B2 | 12/2010 | Lebel et al. |
| 6,475,180 | B2 | 11/2002 | Peterson et al. | 2001/0031944 | A1 | 10/2001 | Peterson et al. |
| 6,485,465 | B2 | 11/2002 | Moberg et al. | 2001/0034502 | A1 | 10/2001 | Moberg et al. |
| 6,489,896 | B1 | 12/2002 | Platt et al. | 2002/0004015 | A1 | 1/2002 | Carlisle et al. |
| 6,500,151 | B1 | 12/2002 | Cobb et al. | 2002/0004645 | A1 | 1/2002 | Carlisle et al. |
| 6,519,569 | B1 | 2/2003 | White et al. | 2002/0128606 | A1 | 9/2002 | Cowan et al. |
| 6,544,229 | B1 | 4/2003 | Danby et al. | 2002/0165491 | A1 | 11/2002 | Reilly |
| 6,554,822 | B1 | 4/2003 | Holschneider et al. | 2003/0009133 | A1 | 1/2003 | Ramey |
| D474,837 | S | 5/2003 | Gillespie, Jr. et al. | 2003/0060754 | A1 | 3/2003 | Reilly et al. |

| | | | |
|---|---|---|---|
| 2003/0060768 A1 | 3/2003 | Kiyatake et al. | |
| 2003/0065287 A1 | 4/2003 | Spohn et al. | |
| 2003/0073954 A1 | 4/2003 | Moberg et al. | |
| 2003/0078534 A1 | 4/2003 | Hochman et al. | |
| 2003/0097092 A1 | 5/2003 | Flaherty | |
| 2003/0149402 A1 | 8/2003 | Gerlach et al. | |
| 2006/0173412 A1 | 8/2006 | Susi | |

FOREIGN PATENT DOCUMENTS

| | | |
|---|---|---|
| EP | 0447985 | 9/1991 |
| EP | 0522527 | 1/1993 |
| EP | 0560270 | 9/1993 |
| EP | 0567944 | 11/1993 |
| EP | 0567945 | 11/1993 |
| EP | 0567946 | 11/1993 |
| EP | 0567962 | 11/1993 |
| GB | 2190145 | 11/1987 |
| GB | 2208897 | 4/1989 |
| GB | 2336510 | 10/1999 |
| WO | WO84/04685 | 12/1984 |
| WO | WO92/03656 | 3/1992 |
| WO | WO93/05829 | 4/1993 |
| WO | WO95/17913 | 7/1995 |
| WO | WO00/42911 | 7/2000 |
| WO | WO00/48112 | 8/2000 |
| WO | WO00/68766 | 11/2000 |

OTHER PUBLICATIONS

International Search Report for International Application No. PCT/US 02/36964 of Applicant Baxter International Inc.

International Search Report for International Application No. PCT/US2010/062150 of Applicant Baxter International Inc.

Written Opinion in PCT Application PCT/US2010/062150, mailed Jul. 21, 2011 (9 pages).

Haydon Switch & Instrument, Inc.—Ball Screw—Haydon Leadscrew Assemblies (website) written by http://www.motioncontrol.com/products/index.cfm/Ball=Screw--Haydon-Leadscrew-Asse . . . printed May 12, 2009, 1 pg.

Portescap, A Danaher Motion Company Linear Actuators Data Sheets on GlotbalSpec (website) written by http://motion-controls.globalspec.com/datasheets/729/Portescap printed May 12, 2009, 1 pg.

International Search Report for International Application No. PCT/US2010/062150 of Applicant Baxter International Inc. dated Dec. 22, 2011.

* cited by examiner

SHUTTLE PUMP WITH CONTROLLED GEOMETRY

BACKGROUND

The field of the invention is infusion pumps and relates generally to systems, apparatuses, and methods for pumping or infusing volumes of medical fluids to a patient, typically via an intravenous route.

Infusion pumps are used to infuse drugs and liquids into patients, typically via intravenous lines. While some infusion pumps deal with relatively large volumes, there may be more interest in pumps with a capability of delivering only very small controlled volumes of liquid. The drugs used may be very important, such as analgesics, anesthetics including opiates, anti-inflammatory agents, insulin, anti-spasmodic drugs, antibiotics, chemotherapy agents, cardiovascular drugs, and the like. Many of these drugs are needed in very low doses on a continuous basis, so that the patient has a steady, reliable stream over a long period of time, such as 0.1 ml per hour. If pulses are used, the dosage rate may be measured in terms of nanoliters or microliters per pulse or bolus. Patients thus depend on infusion pumps for reliable, consistent delivery of very small volumes.

Some infusion pumps propel or pump the liquid of interest by admitting a quantity of liquid into a length of tubing and isolating that quantity, as by occluding a valve at an inlet of the tubing. A mechanism then opens a valve at an outlet of the tubing and another mechanism compresses or otherwise massages the length of tubing in question. Since the inlet is blocked by the closed valve, the liquid can only exit through the outlet, with an open valve. This method works. However, there are at least two drawbacks to this method. Present day infusion pumps, using this type of shuttle mechanism, may squeeze the length of tubing by pressing a moving shuttle against a stationary block.

In cross-section, the tube resides in a diamond-shaped groove or pumping chamber formed by the opposed shuttle and block. Typically, the profiles of the shuttle and the block, or stationary portion, are not very well suited for maintaining the tube in an ideal position throughout the entire compression cycle. Because of this, the profile of the shuttle and block do not always achieve full compression of the tube at any given point during the pumping cycle. For example, prior art infusion pumps operate by occluding tubing between a moving shuttle and a stationary block. The tubing is not completely occluded because prior art pumps do not entirely compress the tubing, leaving the ends of the tubing non-occluded. This situation has at least two disadvantages: an unpredictable amount of liquid remains in the tubing, negatively affecting pump accuracy, and full pumping capacity is not utilized. Over-squeezing the tubing to complete the occlusion can adversely affect tubing life, while under-squeezing lessens the pumping capacity and may adversely affect pumping volume control accuracy.

Typically, the inlet valve, shuttle, and outlet valves previously mentioned are operated via a single motor or actuator. The timing of the operation of each is accomplished by a mechanical linkage. Accordingly, each stroke of the shuttle mechanism pumps a fixed amount of fluid. Therefore, it is difficult or impossible to adjust the pumping capacity or other pumping characteristic of the pump.

SUMMARY

An improved infusion pump is provided in several embodiments.

One embodiment is an infusion pump. The infusion pump includes an inlet valve, an outlet valve, and a shuttle including a shuttle stationary portion and a shuttle moveable portion configured for squeezing a length of tubing between the shuttle stationary portion and the shuttle movable portion, wherein the shuttle moveable portion moves toward and away from the shuttle stationary portion to operate the infusion pump, wherein the shuttle stationary portion and the shuttle moveable portion each include a symmetrical groove for holding and squeezing the length of tubing, the groove symmetrical about a central axis of the groove.

Another embodiment is an infusion pump. The infusion pump includes a housing and contained within the housing, an inlet valve, an outlet valve, and a shuttle including a shuttle stationary portion and a shuttle moveable portion configured for squeezing a length of tubing between the shuttle stationary portion and the shuttle movable portion, wherein the shuttle moveable portion moves toward and away from the shuttle stationary portion to squeeze the tubing, wherein the shuttle stationary portion and the shuttle moveable portion each include a base with a symmetric channel for containing the tubing, each of the shuttle stationary portion and the shuttle movable portion including a plurality of transverse ridges and transverse recesses rising from the base and the channel, wherein a height of the ridges above the channel is less than an outer diameter of the tubing.

Another embodiment is a method of pumping an infusate. The method includes the steps of furnishing an infusion pump, the infusion pump including at least one shuttle having a shuttle stationary portion and a shuttle moving portion, wherein the shuttle stationary portion and the shuttle moveable portion each include a base with a symmetric channel and a plurality of ridges and recesses rising from the base and the channel, wherein the ridges on both sides of the channel are symmetrical. The method also includes controlling operation of the infusion pump by entering commands through at least one input to a controller of the pump, pumping infusate by periodically moving the shuttle moveable portion with respect to the shuttle stationary portion, whereby substantially all of an outer circumference of the tubing is in contact with the portions of the shuttle stationary portion and the shuttle moving portion, and sequentially opening and closing at least one valve of the infusion pump to admit the infusate and to allow the infusion pump to pump the infusate.

Another embodiment is a linear shuttle peristaltic pump. The linear shuttle peristaltic pump includes at least one stationary section, the at least one stationary section including a base, a symmetric channel, at least one ridge on a first side of the channel and at least one recess on a second side of the channel, wherein the channel is formed with symmetrical angles on each side of a center of the channel. The pump also includes a plurality of moveable sections, each moveable section including a base, a symmetric channel, a ridge on a first side of the channel and a recess on a second side of the channel, wherein the channel is formed with symmetrical angles on each side of a center of the channel, and wherein the at least one ridge and at least one recess in the at least one stationary section fit into the recesses and ridges of the moveable sections, and wherein when the at least one stationary section and the plurality of movable sections are assembled, the channels form an opening suitable for a length of tubing, whereby substantially all of an outer circumference of the tubing is in contact with portions of the at least one stationary section and portions of the moving sections when the moving sections operate to squeeze the length of tubing, and a plurality of linear actuators connected to the plurality of moveable sections, each of the plurality of linear actuators further including a sensor for reporting a position of the actuator. In another embodiment, the linear actuators are replaced with a single motor and a cam in contact with each of the plurality of moveable sections.

Another embodiment is a method of pumping a liquid. The method includes the steps of providing a linear shuttle peristaltic pump, the pump including a plurality of shuttle stationary sections and a plurality of shuttle moving sections, each of the sections having a symmetric groove with at least one transverse ridge and at least one transverse recess, wherein the ridges and the recesses of the stationary sections fit into matching recesses and ridges of the moving sections, and wherein substantially all of an outer circumference of tubing in the pump is in contact with surfaces of the stationary sections and the moving sections when the tubing is squeezed. The method also includes controlling operation of the linear shuttle peristaltic pump by entering commands through at least one input to a controller of the pump, pumping liquid by sequentially moving the shuttle moveable sections with respect to the shuttle stationary sections, and sequentially opening and closing at least one valve of the infusion pump to admit the infusate and to allow the infusion pump to pump the infusate.

Another embodiment is a geometry-controlled valve. The valve includes a stationary section, the stationary section including a base, a symmetric channel, at least one ridge on a first side of the channel and at least one recess on a second side of the channel, wherein the channel is formed with symmetrical angles on each side of a center of the channel, and a moveable section, the moveable section including a base, a symmetric channel, a ridge on a first side of the channel and a recess on a second side of the channel, wherein the channel is formed with symmetrical angles on each side of a center of the channel, and wherein the at least one ridge and at least one recess in the stationary section fit into the recesses and ridges of the moveable section, and wherein when the stationary section and the movable section are assembled, the channels form an opening suitable for a length of tubing, whereby substantially all of an outer circumference of the tubing is in contact with the portions of the stationary section and the moving section when the moving section operates to squeeze the length of tubing.

Additional features and advantages are described herein, and will be apparent from, the following Detailed Description and the Figures.

DETAILED DESCRIPTION

Figure 1:
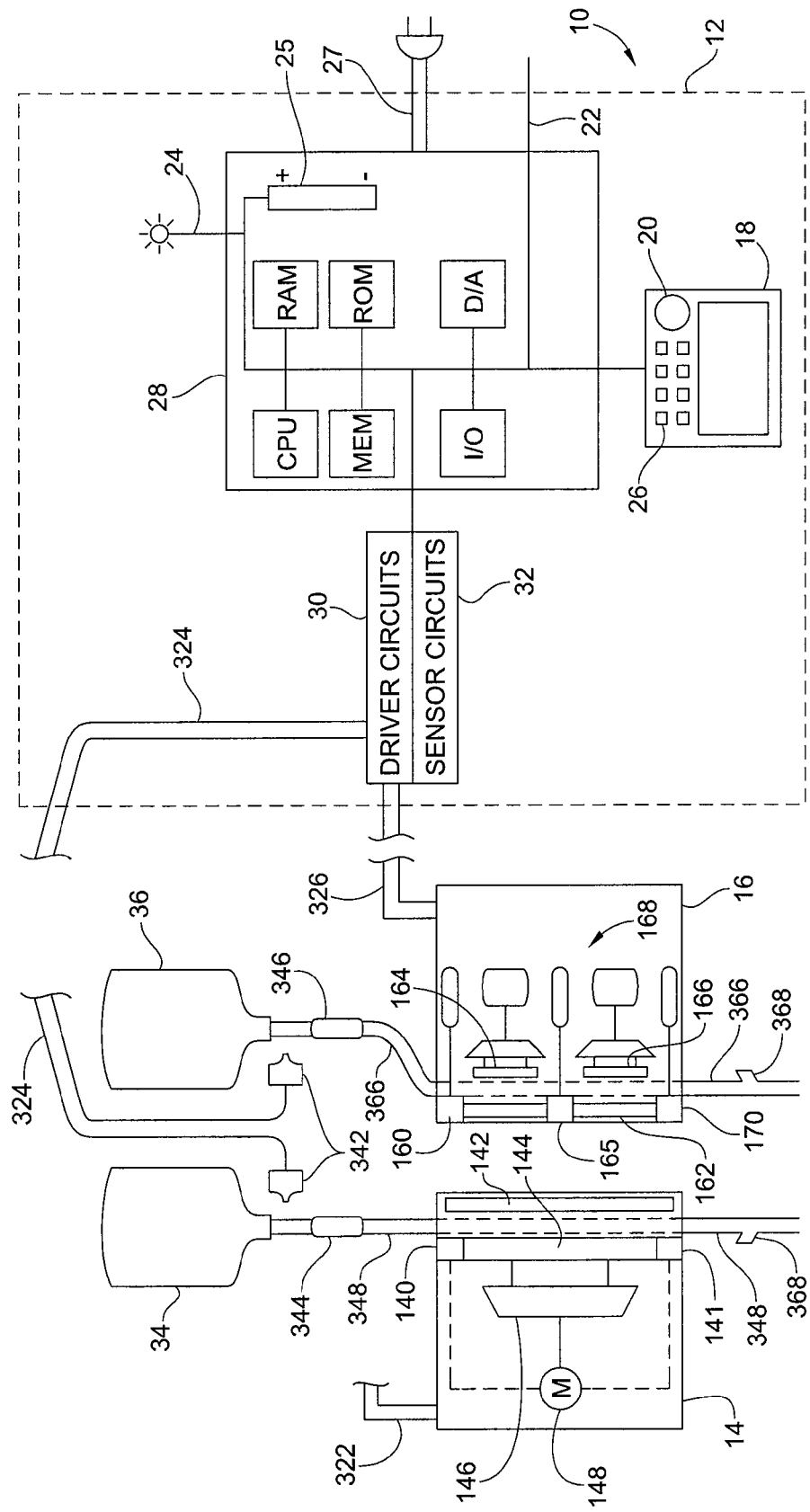
FIG. 1 is a schematic view of an infusion pump controller with two infusion modules.

One embodiment is depicted in FIG. 1. Infusion pump system 10 includes a housing 12 for the infusion pump microcontroller 28, and also includes first infusion pump 14 and second infusion pump 16, a video output 18 and an audio output or speaker 20. The video output 18 is a screen, which may be a touch-screen, allowing for inputs to the microcontroller 28. The infusion pump system 10 also includes inputs 26, which may be conveniently located near screen 18. The infusion pump system 10 includes additional inputs/outputs (I/O), including a landline 22 suitable for cable or other I/O, such as an intranet or cable for a home, a hospital or other care center. There is also an antenna 24 for wireless communication to and from a central monitoring station or other controller (not shown). The infusion pump system 10 includes a battery 25 and may also receive power from an external source via a power cord 27.

The first infusion pump 14 receives liquid from a first container 34 and the second infusion pump 16 receives liquid from a second container 36. The flow of liquid is then conveyed to the respective infusion pump via tubing 348, 366. The tubing 348, 366 in this embodiment is continuous before and after the infusion pumps 14, 16 and extends to an access device connector 368 for each line. The access device connector 368 may be a vascular access device and may be used for administering a drug or other medicament to the patient.

The system controller is a microcontroller 28, which includes a central processing unit (CPU), input/output capability (I/O), digital to analog converter (D/A), and random access memory (RAM) and read-only memory (ROM), and may include additional memory (MEM). A computer program for operating one or more infusion pumps 14, 16 is stored in MEM or ROM. Microcontroller 28 receives inputs from the drip counters 342, to monitor the input to the infusion pumps. The microcontroller 28 also receives inputs from a number of sensors or devices associated with the infusion pumps 14, 16, such as encoder data from rotary encoders on a motor driving the infusion pump, linear voltage displacement transducer (LVDT) data or other position or displacement data from linear actuators, voltage or current readings from temperature or pressure sensors in the infusion pumps 14, 16, and the like. The data may be sent via wire harnesses 322, 324, 326, or may be wireless, such as wireless signals conforming to the ZigBee/IEEE 805.15.4 wireless standard. The data may be received by the microcontroller 28 or the microcontroller 28 may include a separate interface for sensor circuits 32, as shown. The infusion pumps 14, 16 in this embodiment have a separate section for driver circuits 30, for driving or controlling linear actuators, rotary actuators, motors, and the like.

Infusion pump 14 is driven by a motor 148 driving an infusion pump moveable shuttle section 144 by a camming drive train 146. The moveable shuttle section 144 squeezes tubing 348 against the shuttle stationary section 142 to pump the liquid from container 34. Upper valve 140 opens to admit liquid into the tubing 348 and closes when the tubing 348 is full. Lower valve 141 then opens just before the controller 28 commands infusion pump 14 to actuate and cycle the moveable shuttle section 144. With upper valve 140 closed and lower valve 141 open, the liquid is forced through the lower valve and downstream through connector 368. An encoder or other feedback device on motor 148 informs controller 28 of the position of the motor 148, and thus the position of the moveable shuttle section 144, and also allows calculation of volume pumped by the infusion pump 14 by the computer program.

The second infusion pump 16 operates with linear actuators. A linear actuator is a device that develops force and motion, from an available energy source, in a linear manner, as opposed to a device that operates in a rotary manner, as one that receives torque directly from a rotary electric motor. Examples of linear actuators include electric linear solenoids, linear pneumatic actuators, and hydraulic cylinders. Other examples include ball screws and jack screws, and also cylinders actuated by a linear motor. Infusion pumps as described herein place a premium on space and on reliability. While many types of linear actuators may be used, lead screws and stepper motors from and Haydon Switch & Instrument (HSI) of Waterbury, Conn., U.S.A. and from Portescap, West Chester, Pa., U.S.A., have been found useful for the present infusion pump application.

Infusion pump 16 includes a stationary portion 162 and two moveable shuttles 164, 166, as well as three valves 160, 165, and 170, and five linear actuators 168. The commands to the linear actuators 168 and their positions are reported via harness 326 to the driver circuit portion 30 and are also reported to the microcontroller 28. Infusion pump 16 receives liquid from container 36 and drip chamber 346 and pumps via tubing 366. In this embodiment, tubing 366 is a continuous piece of tubing 366 from the drip chamber 346 to connector 368. Valve 165 closes and valve 160 opens to admit liquid into the tubing 366 downstream from valve 160. When this portion of the tubing 366 is full, valve 160 closes, valve 165 opens, and shuttle 164 advances, pumping liquid downstream through valve 165. Shuttle 166 is open to receive the liquid and valve 170 is closed. Then valve 165 closes, valve 170 is opened, and shuttle 166 closes, pumping the liquid downstream to connector 368 and to the patient. While shuttle 166 is closing, shuttle 164 retracts and valve 160 opens, admitting liquid upstream from valve 165. The process is then repeated, with sequential advance and retraction of the shuttles and appropriate opening and closing of the valves.

The use of two shuttles smoothes the pumping process, so that part of the tubing is being pumped (emptied) while the remainder is being filled. When the first shuttle 164 pumps, the contents of the upper portion of the tubing 366 are discharged into the lower portion of the tubing 366 adjacent the second shuttle 166. When the second shuttle 166 is pumping liquid to the patient, the tubing adjacent the first shuttle 164 is being re-filled. The tubing is quickly filled because the liquid has only to traverse the tubing immediately adjacent the first shuttle 164. Using this technique, a smooth, virtually continuous flow is achieved. In this embodiment, intermediate valve 165 acts as both the outlet valve for upper shuttle 164 and as input valve for lower shuttle 166.

Figure 2:
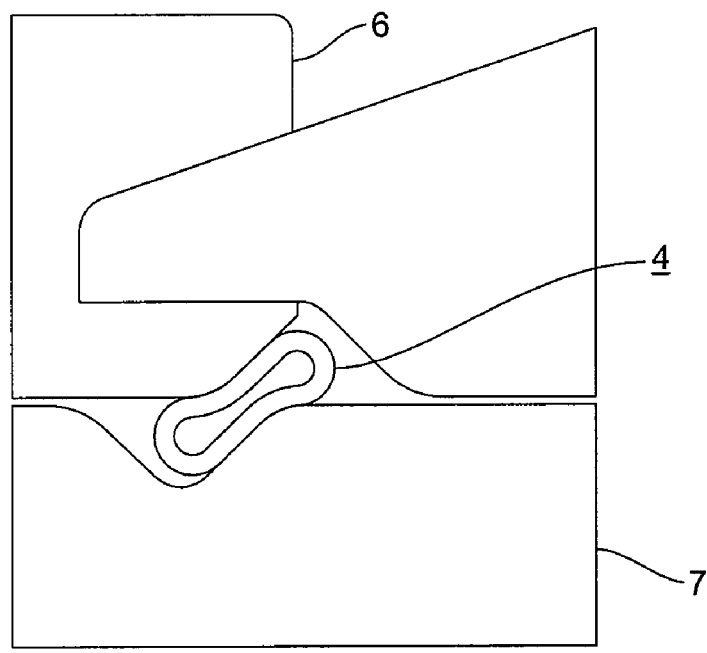
FIG. 2 is a partial cross-section of a prior-art infusion pump geometry.
Figure 3:
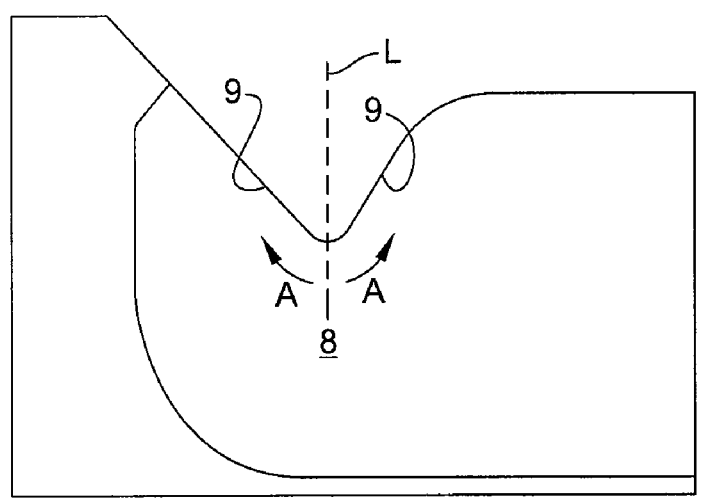
FIG. 3 is a partial cross-section of a profile view of a new infusion pump shuttle geometry.
Figure 4A:
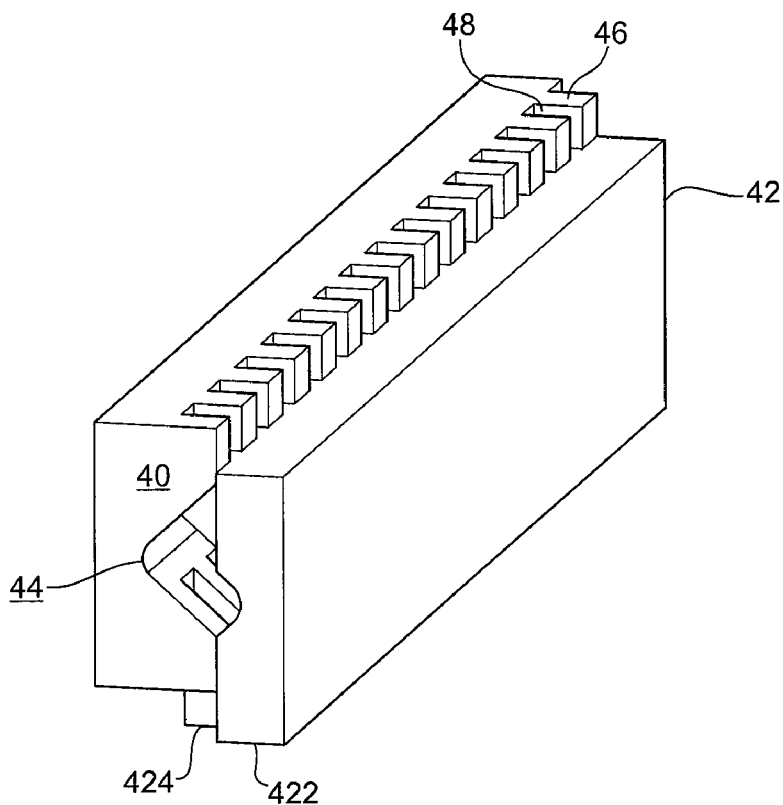
FIGS. 4A and 4B are perspective views of an improved shuttle pump geometry.
Figure 4B:
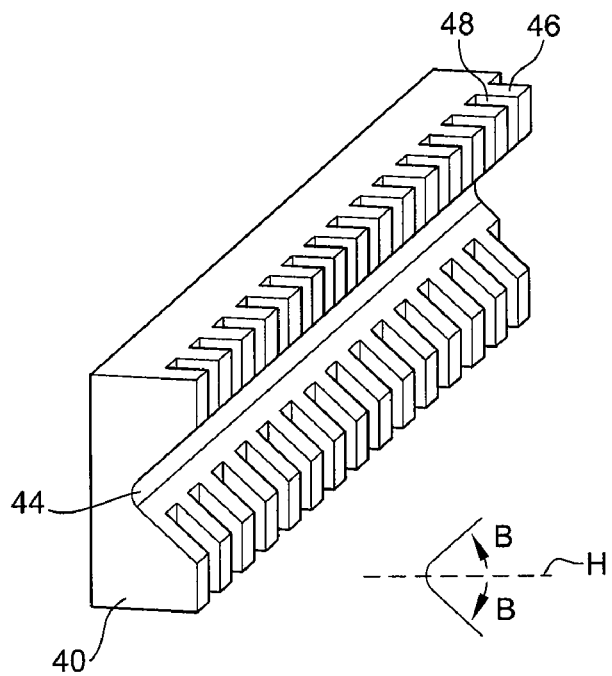

Prior art infusion pumps, such as the one shown in cross-section in FIG. 2, do not uniformly squeeze the tubing 4. Instead, an upper shuttle 6 and a lower stationary portion 7 may tend to compress the tubing so that a small amount of liquid may be left in the tubing, as seen in FIG. 2, thus contributing to inaccuracy in the operation of the infusion pump. In one embodiment of the infusion pump disclosed herein, shown in FIG. 3, the infusion pump has a central groove 8 that is symmetrical with respect to a center line L of the groove, with equal angles A on both sides 9 of the groove, 8. In one embodiment, the corner so formed has a gentle radius from about 0.020 inches to about 0.060 inches (about 0.50 mm to about 1.5 mm). A first embodiment of an improved shuttle pump made of a stationary block 40 and a moving shuttle 42 is depicted in FIGS. 4A and 4B.

The block 40 and the shuttle 42 are each made of a base with a plurality of alternating ridges 46 and recesses 48, with a central channel 44. The ridges 46 of one portion fit into the recesses 48 of the other, allowing sliding movement of the moving shuttle 42 with respect to the stationary block 40. The central channel 44 is configured for receiving a length of tubing, and should have a generous radius and be free from nicks and burrs. The ridges 46 rise perpendicularly from the base at the top and bottom edges of block 40 and shuttle 42, but form an angle B to the central channel of about 45 degrees. In this embodiment, the angles B and the channel are symmetrical with respect to a horizontal plane H bisecting the central channel, i.e., angles B are equal. The sum of the two angles B is from about 60 degrees to about 120 degrees. The tubing will be held or contained in a symmetrical manner, helping to insure that the tubing is not distorted when pumping takes place.

Figure 5A:
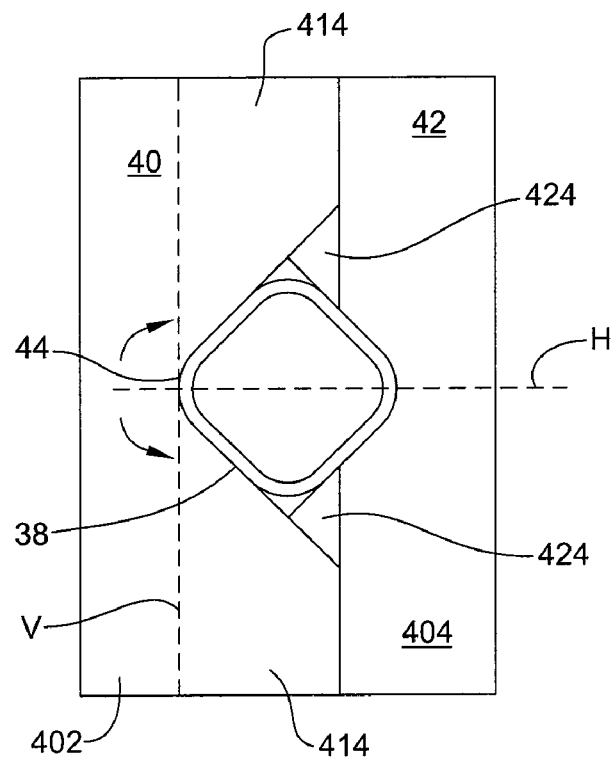
FIGS. 5A and 5B are partial cross-sectional views depicting filling and pumping phases of a shuttle pump with the improved geometry.
Figure 5B:
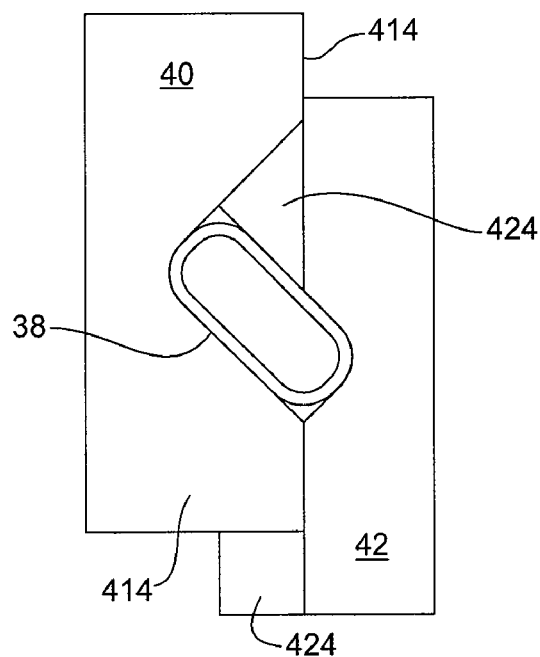

FIGS. 5A and 5B depict a cross-section of the joined stationary and moving portions. In FIG. 5A, the stationary block 40 and moving shuttle 42 are aligned, exerting slight pressure on tubing 38, which is contained within the area as shown between the block 40 and the shuttle 42, with only sufficient pressure to deform normally round tubing 38 into the slightly compressed state shown. FIG. 5A depicts ridges 424 from shuttle 42, which fit into recesses (not shown) of the block 40. Tubing 38 rests in the open area and is symmetrical with respect to the horizontal plane H. Vertical plane V is perpendicular to the horizontal plane and is taken at the locus of the corner or central channel 44. As seen in FIG. 5A, about three-fourths of the diameter of tubing 38 is contained within the block 40, while about one-fourth extends about the top (right) surface of shuttle 42.

As seen in FIG. 5B, the left and right portions, block 40 and shuttle 42, match and overlap, and about three-fourths of the diameter of tubing 38 is also contained within the open area of shuttle 42. The radius of the corner or central channel 44 in one embodiment is about 0.030 inches (about 0.75 mm). Base 402 of block 40 is the portion to the left of the vertical plane V. The base 404 of the shuttle 42 is similarly defined, but is to the right to of a vertical plane taken from the locus of its central channel. Block 40 has ridges 414 extending from its base 402, while shuttle 42 has ridges 424 extending from its base 404. In FIG. 5B, shuttle 42 has moved downward to squeeze the tubing 38 and pump the liquid infusate within the tubing 38 to the patient. Tubing 38 is deformed within the space, but with this geometry, the entire outer circumference or periphery of the tubing 38, adjacent to ridges 414, 424 is constrained between the matching ridges 414 of the block 40 and ridges 424 of the shuttle 42.

Figure 6:
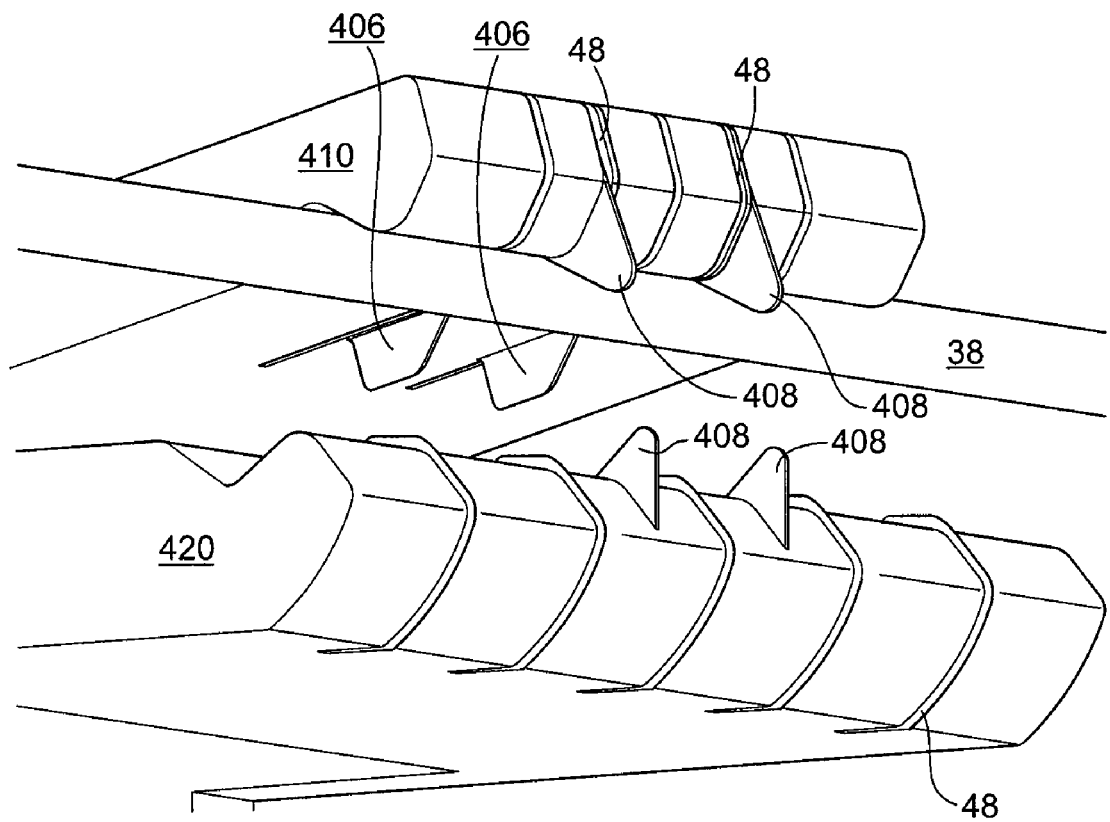
FIG. 6 is a perspective view of another shuttle design.

Another embodiment of a block 410 and a shuttle 420 are shown in FIG. 6. The block 410 and shuttle 420 are configured to accommodate and squeeze tubing 38 between them. In this embodiment, fingers 406, 408 are added on both the block 410 and the shuttle 420 to help secure and squeeze the tubing 38. In block 410, rear fingers 406 and front fingers 408 are positioned adjacent the tubing 38 to fit into matching slots 48 in shuttle 420. The fingers 406, 408 push against the tubing 38 and help to contain and squeeze the tubing 38 when the shuttle 420 contacts the tubing 38 by squeezing it against block 410. In this depiction, shuttle 420 has rotated downward and away from contact with the tubing 38 and fingers 406, 408 in the block 410 are shown in contact with tubing 38. Shuttle 420 also has rear fingers 406 (not shown), and front fingers 408 for performing the same function, containing and squeezing the tubing 38, on the other side of the tubing. The fingers 406, 408 on shuttle 420 fit into matching slots or recesses 48 on block 410.

Figure 7:
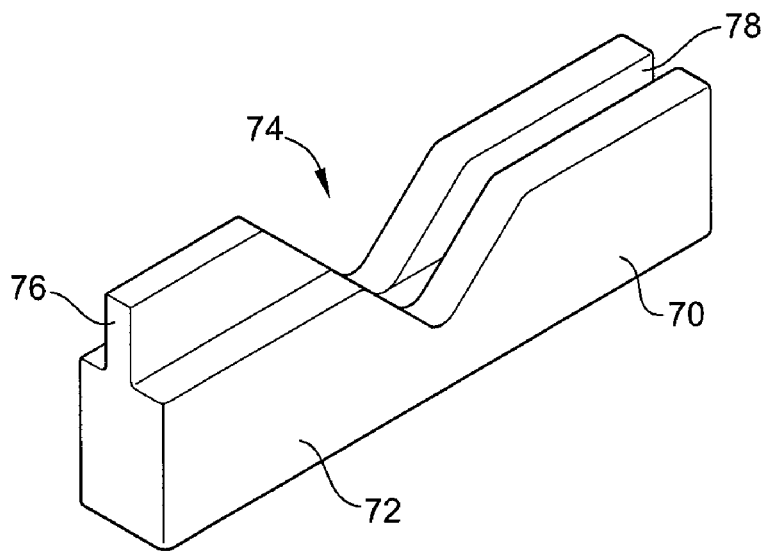
FIG. 7 is a perspective view of another shuttle geometry design.
Figure 8:
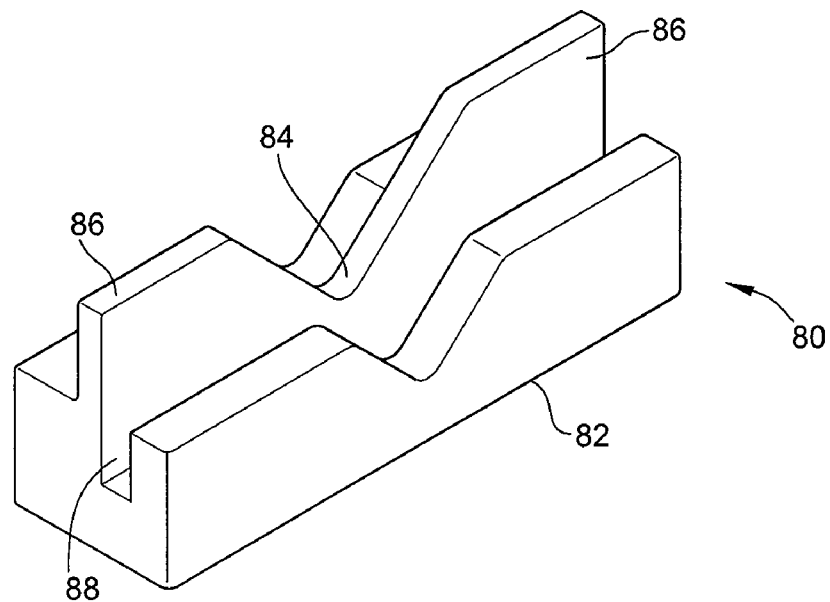
FIG. 8 is a perspective view of yet another shuttle geometry design.

The block 410 and shuttle 420 described above may also be made and used in smaller portions for occluding the tubing 38. For example, instead of squeezing a longer portion of the tubing 38 for pumping, a much shorter version may be used as a valve. FIGS. 7 and 8 depict an example. In FIG. 7, occluder 70 may be used as the stationary portion or block, or alternatively may be used as the moving portion or shuttle, of a valve to occlude tubing. Occluder 70 is similar to the stationary and moving portions described above. Occluder 70 includes a base portion 72, a central channel 74, a single ridge 76 and a single recess 78. The occluder 70 shown is used with a matching occluder 70 atop occluder 70, with the ridge 76 of one occluder 70 placed into the recess 78 of the other, and vice versa. By sliding or maneuvering one occluder 70 back and forth, a length of tubing may be opened and closed, thus allowing and ceasing flow of liquid in an infusion pump. This configuration has the same advantages as the shuttle pumps discussed above, in that the entire circumference or periphery of the tubing is occluded and is less likely to be subjected to excessive pressures, leading to premature failure.

Another embodiment of an occluder that is capable of acting as a valve is depicted in FIG. 8. In this embodiment, occluder 80 with base portion 82 includes two ridges 86 and two recesses 88, a ridge 86 and a recess 88 on each side, the positions of the two reversed across the transverse central channel 84. The embodiment is intended for use with two occluders 80, one stationary and one moving, as with occluders 70, block 40 and shuttle 42. In addition, since both occluder embodiments 70, 80 may also be used to push liquid from the tubing, they may be used to pump the liquid.

Figure 9:
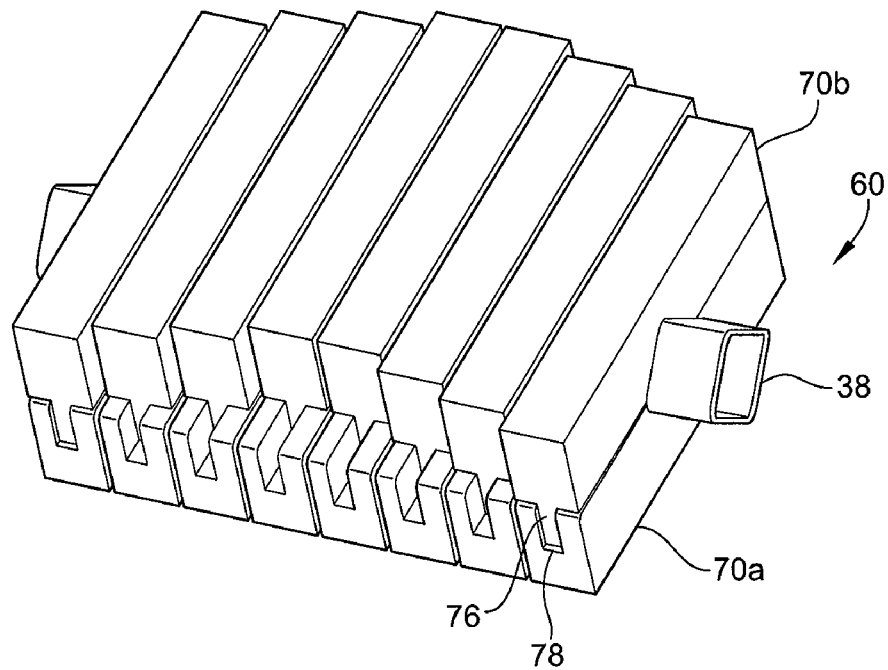
FIG. 9 is a perspective view of another application of the improved shuttle design.

FIG. 9 depicts an embodiment in which a plurality of occluder sections 70 are used for both the stationary and moving portions of a linear peristaltic pump 60. In the figure, several stationary sections 70a are placed adjacent each other, their recesses 78 visible and accommodating ridges 76 from a matching number of identical moving portions 70b placed atop the stationary sections 70a. The moving portions 70b are portrayed as staggered, as would be the sections of a linear peristaltic pump 60. The moving sections 70b move in sequence, with a fixed small volume of liquid passing from one to another as each section 70b closes to pass the volume to the next and then opens to receive another small volume. The sections 70b are movable by linear actuators, e.g., solenoid actuators or other actuators (not shown). The volume pumped per unit time is variable if the displacement of the actuator is variable. For example, a three-position solenoid may be used to pump volumes in accordance with either of the two possible positions besides the closed position. Linear actuators that can be programmed to move a particular distance may also be used to control pumping volume. Of course, an inlet valve and an outlet valve may also be used with such a linear peristaltic pump 60. It will be understood by those with skill in the art that the linear peristaltic pump 60 of FIG. 9 could also operate with a single stationary portion (not shown), with appropriate ridges 76 and recesses 78, and a plurality of moving portions 70b mounted to the stationary portion. This would make such a pump less expensive and easier to repair.

Figure 10:
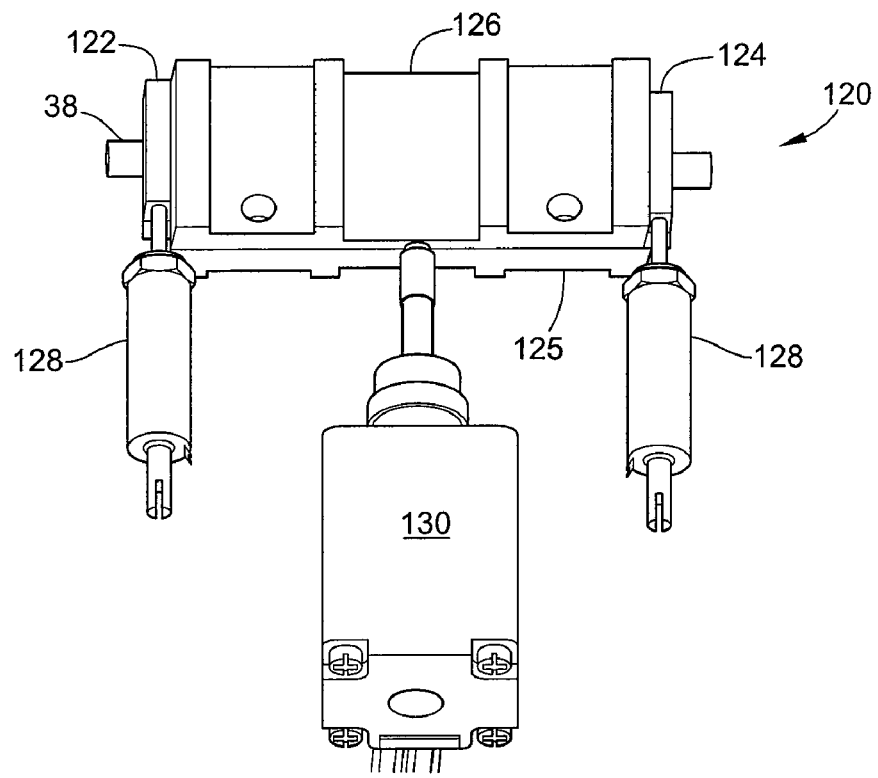
FIG. 10 is a perspective view of an embodiment of a moving shuttle section.
Figure 11:
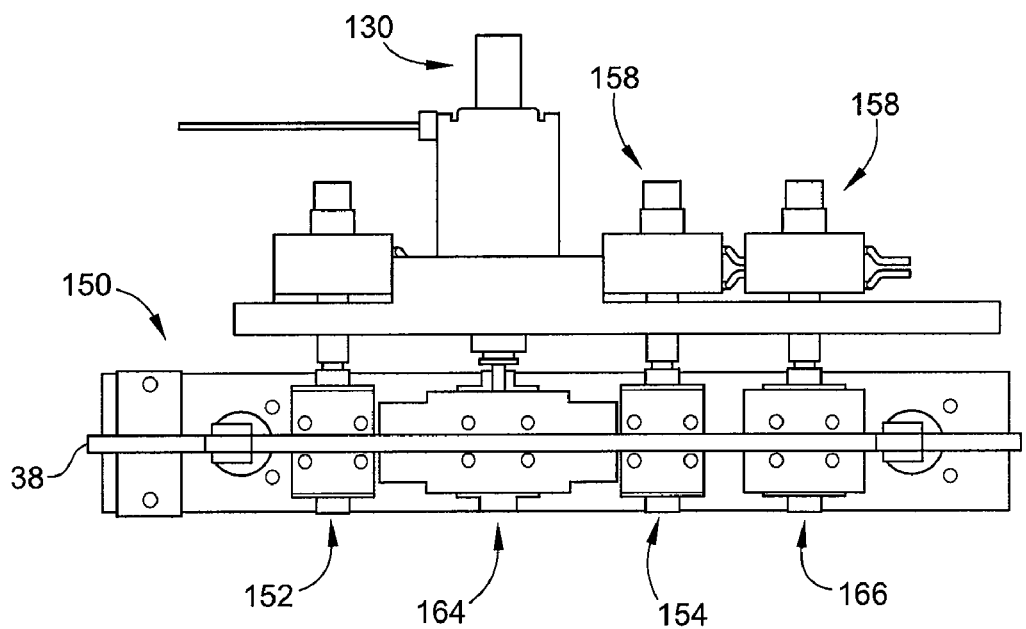
FIG. 11 depicts another embodiment of a shuttle-type infusion pump.

Other linear actuation embodiments are depicted in FIGS. 10 and 11. In FIG. 10, a infusion pump 120 includes an inlet valve 122, an outlet valve 124, a stationary or block section 125 and a shuttle or moving section 126. The infusion pump 120 manipulates tubing 38 to pump infusion liquid. The valves 122, 124 are opened and closed by linear actuators 128, which may be standard, 2-position electric solenoids. The shuttle 126 is moved linearly back and forth by linear actuator 130. The block and shuttle 125, 126 may be similar to those depicted in FIGS. 4A, 4B, 5A and 5B, or may be different. The timing of the valve 122, 124 openings and closings, and the actuation of linear actuators 128, 130, i.e., the pumping, are determined by a controller (not shown), to which the linear actuators 128, 130 are connected, and, in this embodiment, by a computer program in the controller. An infusion pump 120 with a shuttle 126 whose motion is controlled by a linear actuator 130 is known as a linear shuttle infusion pump or, in context, a linear shuttle pump.

FIG. 11 depicts actuation for another infusion pump design with virtually continuous pumping motion. One problem with some designs is that periodically, no fluid is pumped in order to allow the tubing set to fill with more fluid. To eliminate this period of no flow, a second shuttle may be added so that the pump can continue to deliver liquid while the primary shuttle refills. Infusion pump 150 also manipulates tubing 38 to infuse liquid to a patient. In this embodiment, liquid is admitted through inlet valve 152 and is pumped first by primary shuttle 164. Primary shuttle 164 pumps liquid to secondary shuttle 166, which is only about half as long as primary shuttle 164. In this embodiment, there is an intermediate valve 154 between the primary and secondary shuttles 164, 166, but there is no outlet valve.

When the primary shuttle has finished pumping and is being replenished, inlet valve 152 is opened and intermediate valve 154 is closed. The secondary shuttle 166 continues the delivery of the fluid. Later, when the intermediate valve is open and the inlet valve is closed, the primary shuttle pumps fluid and fills the secondary shuttle 166. Since the primary shuttle is twice as long and encounters twice the length of tubing, it pumps about twice as much volume as the secondary shuttle. Other embodiments may be used.

The linear movement of the shuttles and valves described in the above embodiments is easy to understand. However, there are also embodiments in which the tubing for an infusion pump is squeezed or actuated by rotary motion, using a shuttle 420 as depicted in FIG. 6. Thus, while linear-actuated embodiments depicted in FIGS. 7 to 11 have advantages, other embodiments may achieve more uniform pumping using a single motor and one or more cam surfaces in engagement with the moveable shuttles or moveable sections.

Figure 12:
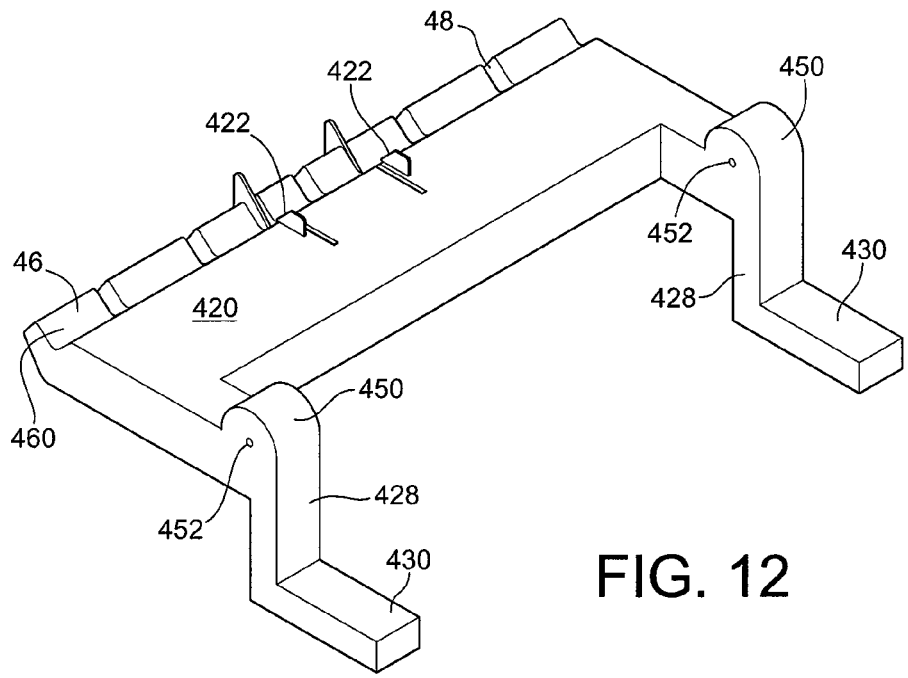
FIG. 12 depicts yet another embodiment of a shuttle-type infusion pump.
Figure 13A:
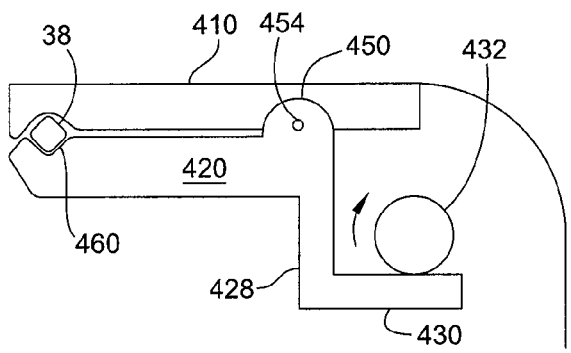
FIGS. 13A and 13B depict infusion pumping by the embodiment of FIG. 6.
Figure 13B:
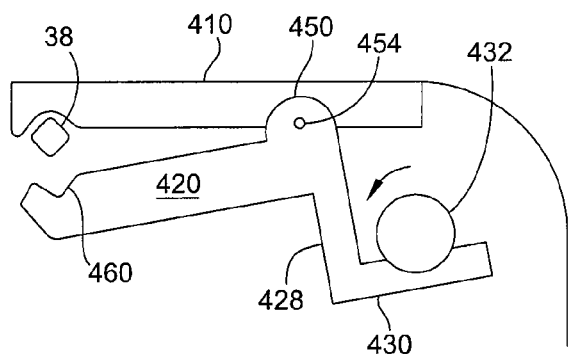

Such an embodiment is further depicted in FIGS. 12, 13A and 13B. Shuttle 420 includes a plurality of ridges 46 and recesses 48, arrayed along a central transverse channel 460. As mentioned above, shuttle 420 may also include fingers 422 for restoring the tubing 38 to an open configuration after an individual pumping sequence has been completed. Shuttle 420 includes a pivot 450 with a bore 452 for a pivot pin 454. The shuttle 420 moves when a motor moves a cam 432 on camming surface 430. The camming surface 430, its movement amplified by lever arm 428, causes shuttle 420 to pivot about pivot 450 and the pivot pin 454, and forcing the ridges 46 against a length of tubing 38, thus pumping liquid and infusing liquid into a patient.

Side views of closed and open positions of this embodiment are further shown in FIGS. 13A-13B. In FIG. 13A, stationary block 410 is fixed in place, as is tubing 38. Shuttle 420 is squeezing tubing 38 in central space 460. Motor rotates cam 432 clockwise against camming surface 430, pressing down on camming surface 430, and through lever arm 428, urging moving shuttle 420 in a clockwise rotation, upwards against the tubing 38. When the liquid in the tube 38 has been pumped, the moving shuttle 420 allows the tubing 38 to open and re-fill with the infusing liquid. In FIG. 13B, cam 438 has rotated counter-clockwise, to allow clockwise pivoting about pivot 450 and pivot pin 454. Tubing 38 can now refill until the next cycle occurs.

Figure 14:
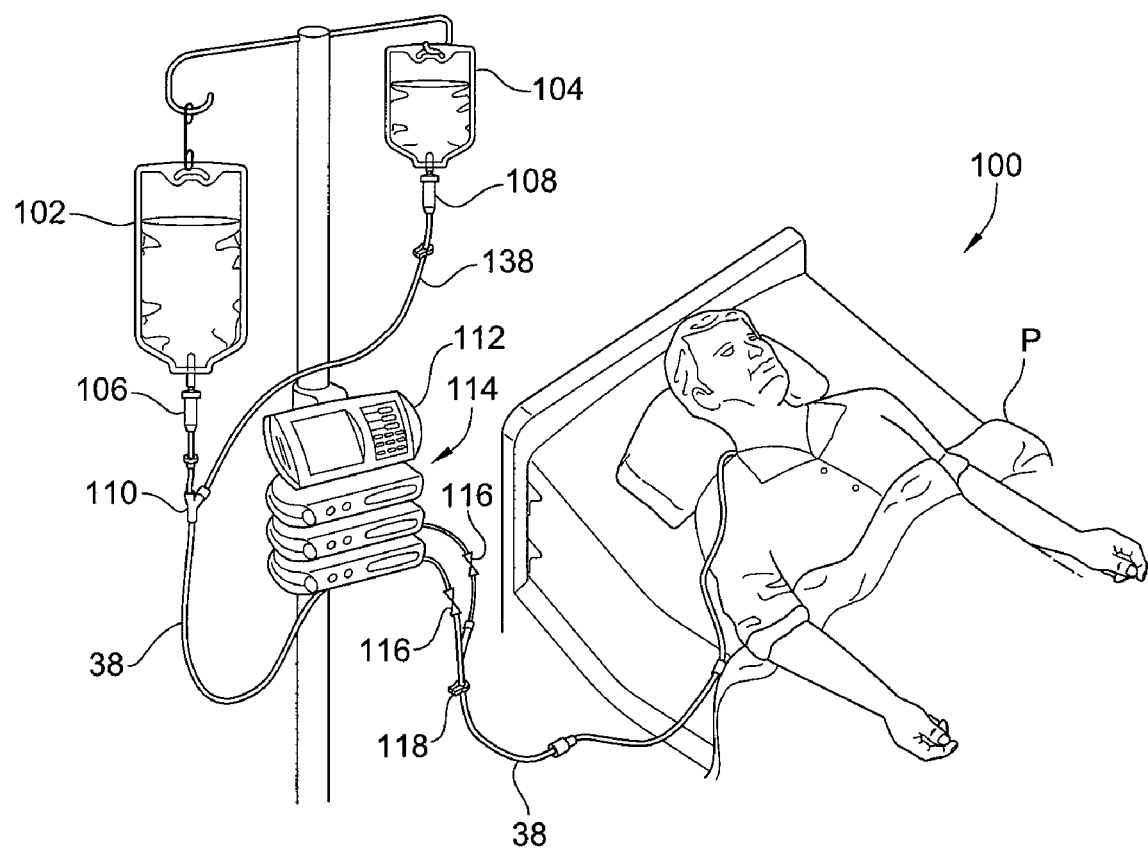
FIG. 14 depicts an application wherein a single controller is used to control and monitor a plurality of infusion pumps for a patient.

FIG. 14 depicts an application with an infusion pump system 100. In this system 100, infusion pump controller 112 controls a plurality of infusion pumps 114, as described above. Each infusion pump 114 receives one liquid for infusing into a patient P, in this instance from containers 102, 104, through drips 106, 108, and IV tubing 38 leading to the respective infusion pumps 114. The tubing 38 optionally has a connector 110, for addition of medicaments to the infusion liquid. The pumped liquid in this embodiment is output from each of the infusion pumps 114 through a check valve 116 and then though another length of IV tubing 38 to the patient P. The IV tubing 38 includes a clamp 118.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An infusion pump, comprising:
an inlet valve;
an outlet valve; and
a shuttle comprising a shuttle stationary portion and a shuttle moveable portion configured for squeezing a length of tubing between the shuttle stationary portion and the shuttle movable portion, wherein the shuttle moveable portion moves toward and away from the shuttle stationary portion to operate the infusion pump, wherein the shuttle stationary portion and the shuttle moveable portion each comprise a symmetrical shuttle groove for holding and squeezing the length of tubing, the shuttle groove symmetrical about a central axis of the shuttle groove and wherein at least one of the inlet valve and the outlet valve comprises a stationary portion and a moveable valve portion, the valve portions each having a valve groove and at least one transverse ridge and at least one transverse recess wherein a height of the at least one ridge above the valve groove is less than an outer diameter of the tubing and wherein the valve portions are configured so that the movable valve portion moves transversely to the length of tubing to occlude the tubing.

2. The infusion pump according to claim 1, wherein the shuttle stationary portion and the shuttle moveable portion each comprise a base and a radiused channel, and where the shuttle stationary portion and shuttle moveable portion each comprise a plurality of transverse alternating ridges and recesses, the ridges of one of the portions fitting into the recesses of the other for interengaged movement to squeeze the tubing.

3. The infusion pump according to claim 1, wherein at least one of the shuttle stationary portion and the shuttle moveable portion further comprises a plurality of extending fingers, wherein the fingers press against the tubing when the shuttle moveable portion moves toward the shuttle stationary portion.

4. The infusion pump according to claim 1, wherein the shuttle stationary portion and the shuttle moveable portion each comprise a base and a radiused channel, and where the shuttle stationary portion and shuttle moveable portion each comprise a plurality of transverse alternating ridges and recesses, the ridges formed at an angle to the base.

5. The infusion pump according to claim 1, wherein the infusion pump includes a plurality of shuttles, the plurality of shuttles configured within the infusion pump to move in sequence to squeeze the length of tubing and pump an infusate.

6. The infusion pump according to claim 5, wherein the plurality of shuttles comprises first and second shuttles, the second shuttle positioned upstream or downstream of the outlet valve.

7. The infusion pump according to claim 1, wherein at least one of the valves or the shuttle is driven by a linear actuator.

8. The infusion pump according to claim 1, further comprising a plurality of fixed fingers in at least one of the shuttle moveable portion and the shuttle stationary portion, each finger protruding from a ridge and extending beyond the ridge, each finger configured for contacting a portion of the circumference of the tubing.

9. The infusion pump according to claim 1, further comprising a linear actuator, wherein the shuttle is actuated by the linear actuator and wherein a volume of infusate pumped by the infusion pump is adjusted by adjusting a stroke of the linear actuator.

* * * * *